United States Patent [19]

Erlich

[11] Patent Number: 5,110,920
[45] Date of Patent: May 5, 1992

[54] HLA TYPING METHOD AND DNA PROBES USED THEREIN

[75] Inventor: Henry A. Erlich, Oakland, Calif.

[73] Assignee: Cetus Corporation, Emeryville, Calif.

[21] Appl. No.: 238,619

[22] Filed: Aug. 30, 1988

Related U.S. Application Data

[60] Division of Ser. No. 678,255, Dec. 5, 1984, which is a continuation-in-part of Ser. No. 456,373, Jan. 7, 1983, Pat. No. 4,582,788, which is a continuation-in-part of Ser. No. 341,902, Jan. 22, 1982, abandoned.

[51] Int. Cl.[5] .................. C12Q 1/68; C07H 15/12; C12N 15/00
[52] U.S. Cl. .................................. 536/27; 435/6; 935/77; 935/78
[58] Field of Search ............... 536/27; 435/6; 935/77, 935/78

[56] References Cited

U.S. PATENT DOCUMENTS 4,582,788  4/1986  Erlich ........................... 435/6

FOREIGN PATENT DOCUMENTS 84796    8/1983  European Pat. Off.
8202060  6/1982  PCT Int'l Appl.

OTHER PUBLICATIONS

Kratzin et al., 1981, Hoppe-Seyler's Z. Physiol. Chem. 362:1665–1669.
Larhammar et al., 1982, Proc. Natl. Acad. Sci. U.S.A. 79:3687–3691.
Wiman et al., 1982, Proc. Natl. Acad. Sci. U.S.A., 79:1703–1707.
Ryder and Svejgaard, 1981, Ann. Genet. 15:169–187.
Kaufman et al., Aug. 1980, J. Exp. Med. 152:37s–53s.
Springer et al., Jul. 21, 1977, Nature 268:213–218.
Stetler et al., 1982, Proc. Natl. Acad. Sci. U.S.A., 79:5960–5970.
Das et al., Mar. 1983, Proc. Natl. Acad. Sci. U.S.A., 80:1531–1535.
Ploegh et al., 1980, Proc. Natl. Acad. Sci. U.S.A., 77:6081–6085.
Larhammar et al., 1981, Scand. J. Imm. 14:617–722.
Sood et al., 1981, Proc. Natl. Acad. Sci. U.S.A., 78:616–620.
Lee et al., Jan. 1982, Proc. Natl. Acad. Sci. U.S.A., 79:545–549.
Robertson, Jun. 24, 1982, Nature 297:629–632.
Roux-Dosseto et al., 1983, Proc. Natl. Acad. Sci. U.S.A., 80:6036–6040.
Auffray et al., 1984, Nature 308:327–333.
Schenning et al., 1984, Embo 3:447–452.
Klein, 1979, Science 203:516–521.

Primary Examiner—Robert A. Wax
Assistant Examiner—Mindy B. Fleisher
Attorney, Agent, or Firm—Kevin R. Kaster; Stacey R. Sias

[57] ABSTRACT

HLA typing based on restriction length polymorphism is carried out by: digesting an individual's DNA with a restriction endonuclease that produces a polymorphic digestion pattern with HLA DNA; subjecting the digest to genomic blotting using a labeled DNA hybridization probe that hybridizes to an HLA DNA sequence involved in the polymorphism; and comparing the resulting genomic blotting pattern with a standard. This technique may be adapted to make paternity or transplant or transfusion compatibility determinations or to make disease association correlations to diagnose diseases or predict susceptibility to diseases. Locus specific cDNA hybridization probes, particularly probes for genes of Class II loci, for use in the typing procedure are described.

9 Claims, 7 Drawing Sheets

← 4.4kb 2.4kb →
2.2kb →

← 2.4kb

HIND III

| | |
|---|---|
| A/D | FATHER |
| E/F | MOTHER |
| D/E | CHILD 1 |
| D/F | CHILD 2 |
| D/E | CHILD 3 |
| A/E | CHILD 4 |
| | INDIVIDUAL X |
| | INDIVIDUAL Y |

PVU II

| | |
|---|---|
| A/D | FATHER |
| E/F | MOTHER |
| D/E | CHILD 1 |
| D/F | CHILD 2 |
| A/E | CHILD 4 |
| D/E | CHILD 3 |

BAM HI

| | |
|---|---|
| A/D | FATHER |
| E/F | MOTHER |
| D/E | CHILD 1 |
| D/F | CHILD 2 |
| D/E | CHILD 3 |
| A/E | CHILD 4 |
| | INDIVIDUAL X |

HLA TYPING METHOD AND DNA PROBES USED THEREIN

CROSS-REFERENCE TO RELATED APPLICATIONS

This application is a division of application Ser. No. 678,255, filed Dec. 5, 1984, which is a continuation-in-part of Ser. No. 456,373 filed 7 Jan. 1983 now U.S. Pat. No. 4,582,788 which in turn is a continuation-in-part of U.S. patent application Ser. No. 341,902 filed 22 Jan. 1982 and now abandoned.

DESCRIPTION

1. Technical Field

The invention is in the fields of genetic engineering and human genotyping. More specifically the invention concerns methods for HLA typing based on HLA DNA restriction fragment length polymorphism (RFLP) and to novel DNA probes that are used in such methods.

2. Background Art

The major histocompatibility complex (MHC) of humans is a cluster of genes occupying a region located on the sixth chromosome. This complex, denoted HLA (Human Leukocyte Antigen), has been divided into five major gene loci, which according to World Health Organization nomenclature are designated HLA-A, HLA-B, HLA-C, HLA-D, and HLA-DR. The A, B, and C loci are single gene loci. The D and DR loci are multi-gene loci. The A, B, and C loci encode the classical transplantation antigens, whereas the D and DR loci encode products that control immune responsiveness. More recent definitions divide the gene products of the HLA loci into three classes (I, II, and III) based on structure and function (*Nature* (1982) 297:629–632). Class I encompasses the products of the HLA-A, HLA-B, and HLA-C loci and the Qa/TL region. The products of the HLA-D and HLA-DR related genes fall in Class II. The Class II antigens are believed to be heterodimers composed of an $\alpha$ (~34,000 daltons) glycopeptide and a $\beta$ (~29,000 daltons) glycopeptide. The number of loci and the gene order of Class II are tentative. Class II currently includes loci designated DR$\alpha$, DR$\beta$, DC$\alpha$, DC$\beta$, SB$\alpha$, and SB$\beta$. Thus far, there appear to be 6$\alpha$ loci and 7$\beta$ loci, based on recent molecular studies. It is possible that future investigation at the DNA level will reveal additional Class II loci. The third class, Class III, includes components of complement. As used herein, the term "HLA" is intended to include the above described loci as well as loci that are closely linked thereto.

The products encoded by the HLA loci are currently typed serologically or by mixed lymphocyte culture methods. Such typing is used in paternity determinations, transplant and transfusion compatibility testing, blood component therapy, anthropological studies and in disease association correlation to diagnose diseases or predict susceptibility to diseases. The major drawbacks to such HLA typing, particularly of the Class II loci, are the complexity of the sera and the lack of widespread availability of standard sera necessary to conduct the tests.

In addition, since the class II antigens are expressed on B but not T lymphocytes, such serologic typing requires physical separation and discrimination between the B lymphocytes and other cells present in peripheral blood. Given the genetic complexity of the class II loci, as revealed by DNA analysis, the nature of the antigenic determinants recognized by HLA-DR typing sera remains ill-defined. Also, serologically indistinguishable DR types show variability defined by biochemical studies (2D gel electrophoresis of $\beta$ chains), by cellular typing, and by DNA analysis (RFLP). Also, since serological typing is based on reactions of sera with the HLA gene products it may not be useful for fetal HLA typing in the early stages of pregnancy when those products have not yet been expressed. Further, the lymphocytotoxicity test often gives results that do not provide an adequate basis for recognizing Class II locus specificities (DR blanks).

It is well known that there is extensive polymorphism in the DNA of the human population. Recent work has also found polymorphism in the restriction endonuclease digests of human DNA. Restriction endonucleases recognize specific nucleotide sequences in DNA and catalyze endonucleolytic cleavages, yielding DNA fragments of defined length. Differences among individuals in the lengths of a particular restriction fragment are called "restriction fragment length polymorphisms". Kan and Dozy *PNAS*, (1978) 75:5631–5635 report RFLPs produced by HpaI cleavage of human $\beta$-globin genes and an apparent association between a 13.0 kb variant of the normal 7.6 kb fragment and sickle hemoglobin mutation. These RFLPs were detected by comparing Southern blots of HpaI restricted cellular DNA from individuals with normal hemoglobin, sickle cell trait, and sickle cell anemia probed with a radiolabeled $\beta$-globin cDNA probe.

Botstein, et al, *Am J Human Genet* (1980) 32:314–331, have proposed using RFLPs as genetic markers to construct a genetic linkage map of the human genome. Their proposal contemplates identifying polymorphic loci by Southern blotting using restricted DNA and random genomic DNA probes, testing the loci for linkage relationships in human pedigrees, and arranging the loci into linkage groups to form a genetic map. None of the reported probes map to the HLA region.

Sood, et al, *PNAS* (1981) 78:616–620 (also PCT application 8202060 published 24 June 1982), describe the isolation of cDNA clones for HLA-B antigens. These clones were prepared by synthesizing cDNA from an mRNA mix containing mRNA coding for the desired HLA antigen, inserting the cDNA into a vector, transforming a bacterial host and isolating transformant clones that contain the desired DNA segment by probing with an oligonucleotide probe that is specific for the desired DNA sequence Ploegh, et al, *PNAS* (1980) 77:6081–6085 have also reported cloning a cDNA probe for an HLA gene sequence.

DISCLOSURE OF THE INVENTION

One object of the invention is to provide a method of typing the HLA system based on HLA DNA restriction fragment length polymorphisms. Encompassed within this method are specific techniques of evaluating paternity and transplant or transfusion compatibility and for diagnosing disease susceptibility.

A second object of the invention is to provide novel HLA DNA probes for use in the typing methods. Such probes include new locus specific probes, particularly for Class II loci.

The basic typing method comprises:

(a) digesting HLA DNA from an individual with a restriction endonuclease that produces a polymorphic digestion pattern with HLA DNA;

(b) subjecting the digest of (a) to genomic blotting using a labeled DNA hybridization probe that hybridizes to an HLA DNA sequence involved in the polymorphism; and (c) comparing the genomic blotting pattern obtained in (b) with a standard genomic blotting pattern for said HLA DNA sequence obtained using said restriction endonuclease and an equivalent labeled DNA hybridization probe. As used in connection with describing the probe the term "equivalent" is intended to mean the same probe or one having the same specificity.

In an alternative embodiment of the invention the blotting step is replaced by a solution hybridization of the digest with the probe followed by resolution of the hybridizate. The resolution pattern is compared to a standard resolution for the HLA DNA sequence obtained using the same restriction endonuclease and an equivalent probe.

Identifying a specific HLA locus by this method involves using a restricion endonuclease that produces a polymorphic digestion pattern of the particular HLA locus and a DNA hybridization probe that is specific to the HLA locus sequence.

As applied to paternity testing the method involves:

(a) digesting HLA DNA of the mother of the individual, the suspected father of the individual, and the individual with a restriction endonuclease that produces a polymorphic digestion pattern for HLA DNA;

(b) subjecting each of the digests of (a) to genomic blotting using a labeled DNA hybridization probe that hybridizes to an HLA DNA sequence involved in the polymorphism; and (c) comparing the genomic blotting patterns obtained in (b) to determine correspondence between the individual's patterns and the mother's and suspected father's pattern and thereby determining whether the suspected father is the actual father of the individual.

A fragment present in the child, absent in the mother, and absent from the alleged father, would constitute an exclusionary result. If such a fragment is, in fact, present in the alleged father, the inclusionary probability can be calculated based on the frequency of the particular restriction fragment in the population. By analyzing several different fragments, possibly with different probes and enzymes, the inclusionary probabilities attainable should be higher than those achieved by current serologic techniques. The more probes and enzymes used, the higher the inclusion probability attainable with the present invention.

Use of the method for determining transplant or transfusion compatibility may be carried out in a manner similar to that used in paternity testing except that HLA DNA of the host and donor are analyzed and compared.

Use of the method in disease susceptibility prognosis involves comparing the individual's pattern (including individual restriction fragments) with a standard pattern that is associated with the disease.

The novel DNA hybridization probes of the invention are HLA locus specific. These locus specific probes comprise labeled DNA sequences that hybridize specifically to the DNA sequence in a given locus.

MODES FOR CARRYING OUT THE INVENTION

Figure 1:
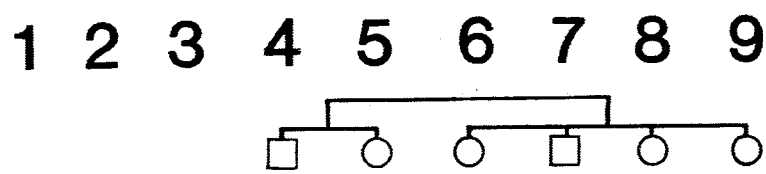
FIG. 1 is the autoradiograph described in Example 6.
Figure 1:

The initial step in typing an individual's HLA by the invention method is to obtain a sample of the individual's DNA. As used herein, the term "individual" is intended to include beings that are in a fetal stage. All nucleated cells contain HLA DNA and, therefore, are potential sources for the required DNA. For convenience peripheral blood cells will typically be used rather than tissue samples. As little as 5 to 100 cc of peripheral blood provide sufficient HLA DNA for typing. In the case of fetal HLA typing, placental cells, chorionic villus biopsies, or amniotic fluid may be used. The DNA is isolated from nucleated cells under conditions that preclude DNA degradation. Such isolation involves digesting the cells with a protease that does not attack DNA at a temperature and pH that reduces the likelihood of DNase activity followed by extraction of the digest with a DNA solvent. DNA isolation from nucleated cells is described by Kan, et al, *N Eng J Med* (1977) 297:1080-1084 and *Nature* (1974) 251:392-393, and Kan and Dozy, supra. The extracted DNA may be purified by dialysis, chromatography, or other known methods for purifying polynucleotides.

In the second step of the method the isolated DNA is restricted with a restriction endonuclease that cleaves or cuts DNA hydrolytically at a specific nucleotide sequence. Sequences so recognized by the enzymes are called restriction sites. Restriction endonucleases that recognize and cleave at specific sites are sometimes referred to as class II restriction enzymes (class I enzymes cleave randomly rather than at specific sites). Enzymes that produce blunt end DNA fragments (hydrolysis of the phosphodiester bonds on both DNA strands occur at the same site) as well as enzymes that produce sticky ended fragments (the hydrolysis sites on the strands are separated by a few nucleotides from each other) may be used. In any event, it is essential that the restriction endonuclease be one that produces a polymorphic digestion pattern associated with the HLA locus or loci under investigation. Determinations of which enzymes produce RFLPs at which loci may be made experimentally using various enzymes in conjunction with various specific HLA cDNA probes in the invention method. Table 1 lists the RFLPs that have been identified to date in this manner.

TABLE 1

| HLA cDNA probe | Enzymes revealing RFLP |
| --- | --- |
| pHLA-Dp34 (DRα) | BglII, EcoRV |
| p29G8 (SBα) | BglII |
| pHLA-B7 | EcoRI, PvuII, KpnI, XbaI, HindIII, BamH1 |
| p2918.4 (DRβ) | EcoRI, BglII, TaqI, RsaI, PstI, KpnI, BamHI, HindIII, StuI, SacI, XbaI, PvuII, MspI |
| p2918.8 (DCβ) | EcoRI, BglII, PstI, RsaI, TaqI, KpnI, BamHI, HindIII, StuI, |

TABLE 1-continued

| HLA cDNA probe | Enzymes revealing RFLP |
|---|---|
| | SacI, XbaI, PvuII, MspI |
| DCα | RsaI, TaqI, BamHI, HindIII, XbaI |

The digestion of the DNA with the endonuclease may be carried out in an aqueous medium under conditions favoring endonuclease activity. Typically the medium is buffered to a pH of 6.5 to 8.0. Mild temperatures, 20° C. to 45° C., preferably physiological temperatures, are employed. Restriction endonucleases normally require magnesium ions and, in some instances cofactors (ATP and S-adenosyl methionine) or other agents for their activity. Therefore, a source of such ions, for instance inorganic magnesium salts, and other agents, when required, will be present in the medium. The amount of DNA in the digestion mixture will typically be in the range of 1% to 20% by weight. In most instances 5 to 20 μg of total cell DNA digested to completion provides an adequate sample for typing. Excess endonuclease, usually one to five units/μg DNA, will be used. If desired the restriction digest may be worked up by precipitation and resuspension as described by Kan and Dozy, supra, prior to being subjected to genomic blotting or solution hybridization, as the case may be.

The third step of the process is analyzing the restriction digest by genomic blotting or solution hybridization and resolution for the presence of one or more HLA gene sequences. In the case of typing for a particular HLA gene the analysis is directed to detecting a DNA sequence that uniquely characterizes that gene. However, when the invention is used for paternity testing or transplant or transfusion compatibility the analysis does not necessarily involve identifying a specific locus or loci but may be done by comparing single or multilocus patterns of one individual with that of another individual using the same restriction endonuclease and an equivalent probe to determine similarities and differences between the patterns. In this regard a single locus probe will identify RFLPs associated with a single HLA locus (it hybridizes to the DNA at only a single locus) whereas a mutilocus probe will identify RFLPs associated with two or more HLA loci (it hybridizes to DNA at a plurality of loci). Three basic steps are involved in the analysis: (1) resolving or separating the fragments by size; (2) annealing the fragments with a labeled DNA probe that hybridizes to the desired HLA DNA sequence(s); and (3) detecting the presence of labeled hybrids. The first two steps in the sequence—separating and annealing—are reversed in the solution hybridization embodiment. The genomic blotting embodiment uses the indicated sequence. The analysis method known as "Southern blotting" that is described by Southern, E. M., *J Mol Biol* (1975) 98:503–517 is currently a preferred analysis method. In Southern blotting the digestion products are electrophoresed, transferred and affixed to a support which binds nucleic acid, and hybridized with an appropriate labeled DNA probe. Radiolabeled hybrids are detected by autoradiography.

Electrophoresis is the separation of the digestion products contained in a supporting medium by size under the influence of an applied electric field. Gel sheets or slabs, e.g., agarose or agarose-acrylamide, are typically used as the supporting medium in Southern blotting. The electrophoresis conditions are such as to effect the desired degree of resolution of the fragments. A degree of resolution that separates fragments that differ in size from one another by as little as 100 base pairs will usually be sufficient. Size markers are run on the same gel to permit estimation of the size of the restriction fragments. In carrying out the electrophoresis, the digestion products are loaded onto one end of the gel slab, (commonly called the "origin") and the fragments separated by electrically facilitated transport through the gel, with the shortest fragment electrophoresing from the origin towards the other (anode) end of the slab fastest.

After electrophoresis the gel is readied for annealing by placing it in a DNA denaturing solution, conveniently a mild base, generally about 0.2 to 1 M hydroxide, preferably 0.5 M NaOH, to dissociate the DNA strands. After denaturation, the gel is placed in a neutralizing solution and neutralized to a mildly acid pH. The DNA is then transferred to the substrate, which is typically made from materials such as nitrocellulose paper or diazobenzyloxymethyl paper, by contacting the gel with the paper in the presence of reagents, e.g., buffer, and under conditions, e.g., light weight and 0° C. to 25° C., that promote transfer and covalent or noncovalent binding of the DNA (particularly guanosine and uridine bases) to the sheets. Such reagents and conditions are described by Southern, E. M., supra, Wahl, et al, *PNAS* (1979) 76:3683–3687, Kan and Dozy, supra, and U.S. Pat. No. 4,302,204. After the transfer is complete the paper is separated from the gel and is dried. Hybridization (annealing) of the resolved single strand DNA on the paper to an HLA DNA probe is effected by incubating the paper with the probe under hybridizing conditions. The hybridization will typically be conducted in an aqueous buffer solution containing a polar solvent such as formamide. Other additives that enhance the hybridization such as sodium chloride, sodium citrate, serum albumin and sonicated denatured DNA such as denatured salmon sperm DNA may be included in the hybridization medium. See Southern, supra, Kan and Dozy, supra and U.S. Pat. No. 4,302,204, col 5, line 8 et seq.

DNA probes that are specific to one (locus specific) or more than one (multilocus) particular HLA DNA sequence involved in the polymorphism are essential components of the hybridization step of the typing method. The probe may be composed of cDNA sequences (DNA made by reverse transcription of mRNA), genomic DNA sequences, or synthesized DNA sequences (e.g., made by splicing synthesized oligonucleotide sequences). cDNA sequences are preferred because they are currently the easiest to identify, prepare, and structurally characterize the gene product by nucleotide sequence analysis.

cDNA probes may be identified by screening cDNA libraries with oligonucleotide probes. The base sequences for the synthetic oligonucleotide probes used to screen the cDNA libraries are determined from HLA antigen amino acid sequences using the genetic code. The amino acid sequences may be determined experimentally or from published data e.g., Ploegh, et al, supra and Sood, et al, supra. Amino acids with minimal codon degeneracy are used whenever possible. If the amino acid sequence suggests more than one possible oligonucleotide sequence, all possible oligonucleotide sequences that code for the amino acid sequence are made and tested to determine which results in the best probe. Oligonucleotides having the desired base sequences may be prepared using the known phosphate diester, phosphate triester, or phosphite triester techniques. The phosphate triester method described by Good, et al, *Nucl Acid Res* (1977) 4:2157, is preferred. Blocked nucleotide reagents used in this method are available commercially. The specificity of a synthetic oligonucleotide may be determined by primer extension analysis or by using it as a hybridization probe in "Northern" blot analysis (a technique analogous to the Southern blot method for analyzing mRNA instead of DNA that was developed by Alwine, et al, *PNAS* (1977) 74:5350) of poly(A+) mRNA from a B cell line). Potential locus specific probes may also be identified by hybridizing cDNA library clones with multilocus probes and determining the specificity of the clones that anneal with the multilocus probes.

As more information about the DNA sequences of HLA genes becomes available it will be possible to discern whether there are any sequences that are unique to a particular locus, or perhaps a particular allele. Such information will permit the synthesis of locus specific probes that hybridize only to the unique portion of the gene. In this regard preliminary data have been developed indicating that in the case of the HLA-A and HLA-B loci the distinguishing portions of the genes may lie in the 3' untranslated regions.

The final step in the method is identifying labeled hybrids on the paper (or gel in the solution hybridization embodiment). Autoradiography is currently used to detect radiolabel-containing hybrids. It involves laying the paper on a piece of radiation-sensitive film (X-ray film). The disintegration of the label results in the deposition of a silver grain in the film. The film is developed and the pattern of labeled fragments is identified. Fluorochromes, enzymes, or other marker molecules such as biotin may also be used as labels. The specificity of the probe and the particular restriction endonuclease used will determine the number of fragments that appear in the pattern. Locus specific probes will typically give patterns with fewer bands than the patterns produced using multilocus probes.

As indicated previously these autoradiographs are used to determine HLA type or, in the case of paternity testing, transplant or transfusion compatibility, and disease association, to determine similarities in the autoradiograph patterns of different individuals or similarities between an individual's pattern and a standard pattern, as the case may be. In this regard it will be appreciated that paternity testing and transplant or transfusion compatibility may also be carried out by HLA typing the individuals by the invention method and comparing their HLA types. In HLA typing the fragments(s) appearing on the test autoradiograph is/are compared to the fragment(s) that characterize a particular HLA type to determine correspondence between the respective fragments and thus whether the test subject is that HLA type. This may be done by matching the test autoradiograph with a standard autoradiograph or simply matching the size distribution of the fragment(s) appearing on the test autoradiograph with the size distribution of the fragment(s) for the standard. By evaluating the HLA DNA RFLP patterns for individuals of known (by conventional HLA typing) HLA type it is possible to assign specific restriction fragments to a given HLA locus and correlate them to serological specificity. It is also expected that practice of the invention method will identify hitherto unidentified HLA genes, particularly in Class II. In this manner correlations between restriction fragment patterns and HLA type may and will be made. Such correlations may be used in deciphering test autoradiographs. The method also provides a technique for defining subdivisions of serologically defined HLA types. The use of HLA types in paternity tests, transplantation or transfusion testing and in disease diagnosis and prognosis is described in *Basic & Clinical Immunology*, 3rd Ed (1980) Lange Medical Publications, pp 187–190. Examples of autoimmune or immunodeficiency disorders associated with serologically defined HLA types are diabetes, myasthenia gravis, Graves' disease, thyroiditis, chronic active hepatitis, Addison's disease, multiple sclerosis, rheumatoid arthritis, celiac disease, and systemic lupus erythematosus.

HLA cDNAs identified as potential probes may also be useful in making recombinant clones expressing human HLA antigens. In this connection, cDNA that encodes a given HLA antigen is inserted into an appropriate cloning vehicle (vector) and hosts are transformed with the vehicles. Transformants are isolated and those that produce the desired antigen are cloned. The antigen may be harvested from the clones by conventional methods. Such antigens may be useful for diagnostic purposes, for making anti-HLA antibodies, or for therapy to induce tolerance to HLA antigens.

The following examples further illustrate the various aspects of the invention. These examples are not intended to limit the invention in any manner.

EXAMPLE 1

Preparation of Hybridization Probe for HLA-Dp34 (HLA-DRα):

Four 11-mer oligonucleotides were prepared based on the known $NH_2$-terminal amino acid sequence (Glu, Phe, Tyr, Leu) of positions 11–14 of HLA-Dp34 antigen. The base sequences for the four oligonucleotides were as follows: (1) AGGTAAAATTC, (2) AGGTAGAATTC, (3) AGGTAAAACTC, and (4) AGGTAGAACTC. These sequences are all complementary to the codons for the indicated peptide sequence and were chosen to minimize degeneracy. The ambiguities are located at sequence positions 2, 3, 6, and 9. A G at positions 2 and 3 was chosen to minimize the destabilizing effect of potential mismatched bases (G is capable of forming a wobble pair with U).

Since the four oligonucleotides were complementary to codons for amino acids 11–14, oligonucleotide primed cDNA synthesis on HLA-Dp34 mRNA was expected to generate a product of about 150–200 nucleotides. This estimate was based on a leader sequence of ~75 nucleotides and assumes a 5' untranslated region of 75–125 nucleotides.

The specificities of the four 11-mers were compared by using them individually as primers in cDNA synthesis reactions using membrane-bound B cell mRNA, free B cell mRNA, and T cell mRNA as template. Only the AGGTAGAACTC oligonucleotide primed a cDNA band of ~175 nucleotides which was enriched in reactions on B cell membrane-bound mRNA template. The specificity of this 11-mer oligonucleotide was confirmed by extending the primer in a cDNA synthesis reaction in the presence of a single dideoxy triphosphate and three deoxy triphosphates, an approach which has proved successful in the isolation of the HLA-B7 cDNA clone (Sood, et al, supra). In the presence of dideoxy dATP, a minor cDNA band corresponding to a predicted 18-nucleotide primer extension product was observed. The additional seven nucleotides were determined by the wandering spot sequencing technique to be GGCCTGA. The following two additional nucleotides, AT, were inferred from the Ile codon, giving a nine nucleotide sequence that corresponded to the HLA-Dp34 antigen amino acids at positions 8, 9, and 10.

A 20-nucleotide fragment having the above determined sequence (AGGTAGAACTCGGCCTGAAT) was then synthesized by the triester method. The specificity of the 20-mer as a primer was examined in a cDNA synthesis reaction on poly(A+) mRNA from a B cell line. A major cDNA band, 175 nucleotides long, was synthesized; the nucleotide sequence of the eluted band corresponded to the expected sequence for HLA-Dp34.

The specificity of the 20-nucleotide fragment as a hybridization probe was analyzed on a Northern blot of poly(A+) mRNA. A unique band, at 1,200–1,300 nucleotides, resulted from probing B cell mRNA but not T cell mRNA with the $^{32}$P-labeled 20-mer nucleotide probe. Membrane-bound mRNA was enriched for the mRNA which hybridized to the 20-nucleotide probe.

An HLA-Dp34 cDNA clone was identified in a cDNA library with the above described 20-mer probe as follows. Membrane-bound RNA and free RNA was prepared, using phenol-chloroform extraction in the presence of Vanadyl complexes, from the human lymphoblastoid B cell line, CA. Poly(A+) mRNA, isolated by affinity chromatography with Poly U-Sepharose, was translated in an in vitro rabbit reticulocyte system. The partition of specific mRNAs into the membrane-bound and free fractions was monitored by 2D gel analysis of the $^{35}$S-labeled products of in vitro translation. A double-stranded cDNA library was prepared from the membrane-bound mRNA using reverse transcriptase, DNA Polymerase I, and S1 nuclease. Following tailing with dCTP using terminal transferase, the cDNA was inserted and ligated to preparations of the plasmid pBR322 which had been digested with Pst and tailed with dGTP.

Initial screening of the library was carried out as follows. Duplicate sets (~4,000 clones/set) of Grunstein-Hogness colony filters were prepared. One set was probed with $^{32}$P cDNA made from size fractionated mRNA from the B cell line, CA. Sucrose gradient fractions were translated in an in vitro rabbit reticulocyte system and the $^{35}$S-labeled products analyzed by 2D gel electrophoresis to determine the appropriate fractions. The other set of filters was probed with $^{32}$P cDNA made from mRNA from the T cell line, Molt-4. A subset of about 150 clones, derived from membrane-bound, B cell specific, 12–14s mRNA, was defined by this initial screening.

Plasmid DNA was prepared from 25 pools, each consisting of 5 candidate cDNA clones and analyzed by dot hybridization with the $^{32}$P-labeled 20-nucleotide probe. Pool 14 plasmid DNA hybridized specifically with the probe. Subsequently, the individual members of the pool were tested; cDNA sequences complementary to the hybridization probe were restricted to the clone identified as 18C7.

In Northern blots, the $^{32}$P-labeled 18C7 nick translated probe hybridizes to a B cell mRNA of the same length (about 1,200 to about 1,300 nucleotides) as the band complementary to the 20-nucleotide probe. In genomic blots with DNA from a hamster-human hybrid containing the human chromosomes 6 and 3, the 18C7 probe hybridizes to a unique restriction fragment absent in the hamster parent, mapping the 18C7 DNA sequences to chromosome 6.

A more precise mapping was possible using the cell line 6.3.6 which has a small deletion at a defined site on the short arm of one homologue of the chromosome 6 pair. This deletion variant fails to express the HLA-A, B, C and HLA-DR specificities associated with one chromosome 6 haplotype. In genomic blots (FIG. 1 and Example 4 below), 18C7 hybridizes to two restriction fragments from the parent cell line, presumably from the two chromosome 6's. Only one fragment is observed in DNA from the deletion variant; the other fragment is presumably derived from the chromosome which has been deleted. This result maps DNA sequences complementary to the 18C7 clone to the chromosomal site defined by the 6.3.6 deletion.

The human HLA-D locus is homologous to the mouse I region. In genomic blots with DNA from mouse congenic lines, inbred lines which differ only at the I region, the 18C7 probe hybridized to a restriction fragment that was different with each congenic line. This result maps DNA sequences complementary to the 18C7 clone to the mouse I region and therefore to the human HLA-D locus.

The 18C7 clone was confirmed as being HLA-Dp34 (HLA-DRα) by analyzing its DNA sequence by the Maxam-Gilbert technique (*Methods in Enzymology* (1980) 65:499–560) using the endonucleases PstI, HinfI, TaqI, Sau3A, AvaII, and BglI. The sequence for the coding strand of the HLA-Dp34 clone is given below.

| | | | | |
|---|---|---|---|---|
| ATCATAGCTG | TGCTGATGAG | CGCTCAGGAA | TCATGGGCTA | TCAAAGAAGA |
| ACATGTGATC | ATCCAGGCCG | AGTTCTATCT | GAATCCTGAC | CAATCAGGCG |
| AGTTTATGTT | TGACTTTGAT | GGTGATGAGA | TTTTCCATGT | GGATATGGCA |
| AAGAAGGAGA | CGGTCTGGCG | GCTTGAAGAA | TTTGGACGAT | TTGCCAGCTT |
| TGAGGCTCAA | GGTGCATTGG | CCAACATAGC | TGTGGACAAA | GCCAACCTGG |
| AAATCATGAC | AAAGCGCTCC | AACTATACTC | CGATCACCAA | TGTACCTCCA |
| GAGGTAACTG | TGCTCACGAA | CAGCCCTGTG | GAACTGAGAG | AGCCCAACGT |
| CCTCATCTGT | TTCATCGACA | AGTTCACCCC | ACCAGTGGTC | AATGTCACGT |
| GGCTTCGAAA | TGGAAAACCT | GTCACCACAG | GAGTGTCAGA | GACAGTCTTC |
| CTGCCCAGGG | AAGACCACCT | TTTCCGCAAG | TTCCACTATC | TCCCCTTCCT |
| GCCCTCAACT | GAGGACGTTT | ACGACTGCAG | GGTGGAGCAC | TGAGGCTTGG |

-continued

| | | | | |
|---|---|---|---|---|
| ATGAGCCTCT | TCTCAAGCAC | TGGGAGTTTG | ATGCTCCAAG | CCCTCTCCCA |
| GAGACTACAG | AGAACGTGGT | GTGTGCCCTG | GGCCTGACTG | TGGGTCTGGT |
| GGGCATCATT | ATTGGGACCA | TCTTCATCAT | CAAGGGAGTG | CGCAAAAGCA |
| ATGCAGCAGA | ACGCAGGGGG | CCTCTGTAAG | GCACATGGAG | GTGATGATGT |
| TTCTTAGAGA | GAAGATCACT | GAAGAAACTT | CTGCTTTAAT | GACTTTACAA |
| AGCTGGCAAT | ATTACAATCC | TTGACCTCAG | TGAAAGCAGT | CATCTTCAGC |
| GTTTTCCAGC | CCTATAGCCA | CCCCAAGTGT | GGTTATGCCT | CCTCGATTGC |
| TCCGTACTCT | AACATCTAGC | TGGCTTCCCT | GTCTATTGCC | TTTTCCTGTA |
| TCTATTTTCC | TCTATTTCCT | ATCATTTTAT | TATCACCATG | CAATGCCTCT |
| GGAATAAAAC | ATACAGGAGT | CTGTCTCTGC | TATGGAATGC | CCCATGGGGC |
| TCTCTTGTGT | ACTTATTGTT | TAAGGTTTCC | TCAAACTGTG | ATTTTTCTG |

A $^{32}$P-labeled HLA-Dp34 probe was made from the clone by nick translation.

EXAMPLE 2

Preparation of Hybridization probes for HLA-SBα (Clones p29G8 and pSBα-318)

A HLA-SBα clone, p29G8, was identified by screening the cDNA library of Example 1 with the nick-translated HLA-Dp34 (DRα) probe under hybridization conditions of reduced stringency to allow detection of related but distinct DNA sequences. The hybridization conditions were as follows.

Hybridize in 50% formamide, 5×SSPE (1×SSPE =0.18M NaCl, 10 mM NaH$_2$PO$_4$, 1 mM Na$_2$EDTA, pH 7.0), 0.1% sodium dodecyl sulfate (SDS), 5×Denhardt's (5×Denhardt's=0.1% w/v each bovine serum albumin, Ficoll, polyvinyl pyrollidone), 200 μg/ml sheared denatured salmon sperm DNA, at 37° C. for 24 h with 1×10$^6$ cpm $^{32}$P-labeled HLA Dp34 probe (2×10$^8$ cpm/μg, labeled by nick translation). Wash filters 3×15 min at room temperature in 5×SSPE, 0.1% SDS.

Under conditions of high stringency (wash at 0.1×SSPE, 65° C.), p29G8 hybridizes strongly only to itself. The coding strand of the p29G8 clone was sequenced using the Maxam-Gilbert procedure.

In genomic Southern blots, the p29G8 probe hybridizes to genomic restriction fragments distinct from those which hybridize to the HLA-Dp34 (DRa) probe in DNA from an HLA hemizygous cell line (6.3.6). The genomic blot pattern with DNA from the cell line T5-1 and its HLA hemizygous derivative 6.3.6 indicates that the p29G8 locus maps within the HLA region. Comparison of the amino acid sequence encoded by this clone with published amino acid sequence data for HLA-SB antigen indicated p29G8 is an HLA-SBα clone. A $^{32}$P-labeled probe was made from the clone by nick translation.

The p29G8 probe was hybridized to a λ cDNA library made from mRNA from the β-lymphoblastoid cell line LG2. The cDNA library was constructed by inserting the duplex cDNA ligated to EcoRI linkers into the EcoRI site of the λ gt 10 vector. It hybridized to a clone designated pSBα-318 that is longer than p29G8 and includes the p29G8 sequence. The sequence of pSBα-318 is given below.

pSBα-318 Sequence

AGTCTCATCTGCCTCCACTCGGCCTCAGTTCCTCATCACTGTTCCTGTGCTCACAGTCAT

CAATTATAGACCCCACAACATGCGCCCTGAAGACAGAATGTTCCATATCAGAGCTGTGAT

CTTGAGAGCCCTCTCCTTGGCTTTCCTGCTGAGTCTCCGAGGAGCTGGGGCCATCAAGGC

GGACCATGTGTCAACTTATGCCGCGTTTGTACAGACGCATAGACCAACAGGGGAGTTTAT

GTTTGAATTTGATGAAGATGAGATGTTCTATGTGGATCTGGACAAGAAGGAGACCGTCTG

GCATCTGGAGGAGTTTGGCCAAGCCTTTTCCTTTGAGGCTCAGGGCGGGCTGGCTAACAT

TGCTATATTGAACAACAACTTGAATACCTTGATCCAGCGTTCCAACCACACTCAGGCCAC

CAACGATCCCCCTGAGGTGACCGTGTTTCCCAAGGAGCCTGTGGAGCTGGGCCAGCCCAA

CACCCTCATCTGCCACATTGACAAGTTCTTCCCACCAGTGCTCAACGTCACGTGGCTGTG

CAACGGGGAGCTGGTCACTGAGGGTGTCGCTGAGAGCCTCTTCCTGCCCAGAACAGATTA

CAGCTTCCACAAGTTCCATTACCTGACCTTTGTGCCCTCAGCAGAGGACTTCTATGACTG

CAGGGTGGAGCACTGGGGCTTGGACCAGCCGCTCCTCAAGCACTGGGAGGCCCAAGAGCC

AATCCAGACGCCTGAGACAACGGAGACTGTGCTCTGTGCCCTGGGCCTGGTGCTGGGCCT

-continued pSBα-318 Sequence

AGTCGGCATCATCGTGGGCACCGTCCTCATCATAAAGTCTCTGCGTTCTGGCCATGACCC

CCGGGCCCAGGGGACCCTGTGAAATACTGTAAAGGTGACAAAATATCTGAACAGAAGAGG

ACTTAGGAGAGATCTGAACCAGCTGCCCTACAAACTCCATCTCAGCTTTTCTTCTCACTT

CATGTGAAAACTACTCCAGTGGCTGACTGAATTGCTGACCCTTCAAGCTCTGTCCTTATC

CATTACCTCAAAGCAGTCATTCCTTAGTAAAGTTTCCAACAAATAGAAATTAATGACACT

TTGGTAGCACTAATATGGAGATTATCCTTTCATTGAGCCTTTTATCCTCTGTTCTCCTTT

GAAGAGCCCCTCACTGTCACCTTCCCGAGAATACCCTAAGACCAATAAATACTTCAGTAT

T

EXAMPLE 3

Preparation of DRβ and DCβ cDNA Clones

An 18-mer having the base sequence CCCTGTCTCGCGCACGCA was prepared for use in screening the above-mentioned λ cDNA library. The sequence of the 18-mer was based on the published amino acid sequence for the conserved amino acids 20-25 of the HLA-DRβ chain. The specific 18-nucleotide sequence was chosen from the published sequence of an HLA-DRβ cDNA clone from the Raji cell line (Wiman, et al, *PNAS* (1982) 79:1703-1707). The specificity of the kinased 18-mer probe was tested by hybridization to an RNA blot. The probe hybridized to an RNA species about 1100-1,300 nucleotides long present in B cell RNA and absent from T cell RNA, as expected for the HLA-DRβ mRNA. Hybridization conditions were for 36 h at 37° C. in 4×SSPE with 5×Denhardt's solution, 0.2 mM ethylene diaminetetraacetic acid (EDTA), and 0.1% SDS. Filters were washed in 2×SSPE, 0.1% SDS at room temperature.

The 18-mer probe was hybridized to the λ cDNA library. cDNA inserts from eight 18-mer reactive λ cDNA clones were isolated and subcloned into the EcoRI site of the plasmid vector, pBR328 (Soberon, X., et al, *Gene* (1980) 9:287-305). Two clones designated 2918.4 (originally DRβ-4) and 2918.8 (originally DRβ-8) hybridized to sequences in the HLA region using the genomic blotting technique with the 6.3.6 HLA hemizygous deletion variant described in Example 1. The genomic blot patterns obtained with the 2918.4 and 2918.8 probes were different indicating these clones represent different loci. The clones were sequenced by the Maxam-Gilbert method. The sequences of their coding strands are reported below.

Clone 2918.4

ATGGTGTGTCTGAAGCTCCNTGGAGGCTCCTGCATGACAGCGCTGACAGTGACACTGATG

GTGCTGAGCTNNNNNNNGGCCCCGGCTGGGGACACCCGACCACGTTTCTTGTGGCAGCTT

AAGTTTGAATGTCATTTCTTCAATGGGACGGAGCGGGTGCGGTTGCTGGAAAGATGCATC

TATAACCAAGAGGAGTCCGTGCGCTTCGACAGCGACGTGGGGGAGTACCGGGCGGTTGAG

GAGCTGGGGCGGCCTGATGCCGAGTACTGGAACAGCCAGAAGGACCTCCTGGAGCAGAAG

CGGGGCCAGGTGGACAATTACTGCAGACACAACTACGGGGTTGGTGAGAGCTTCACAGTG

CAGCGCCGAGTTGAGCCTAAGGTGACTGTGTATCCTTCAAAGACCCAGCCCCTGCAGCAC

CACAACCTCCTGGTCTGCTCTGTGAGTGGTTTCTATCCAGGCAGCATTGAAGTCAGGTGG

TTCCGGAACGGCCAGGAAGAGAAGGCTGGGGTGGTGTCCACGGGCCTGATCCAGAATGGA

GATTGGACCTTCCAGACCCTGGTGATGCTGGAAATAGTTCCTCGGAGTGGAGAGGTTTAC

ACCTGCCAAGTGGAGCACCCAAGTGTGACGAGCCCTCTCACAGTGGAATGGAGAGCACGG

TCTGAATCTGCACAGAGCAAGATGCTGAGTGGAGTCGGGGGCTTCGTGCTGGGCCTGCTC

TTCCTTGGGGCCGGGCTGTTCATCTACTTCAGGAATCAGAAAGGACACTCTGGACTTCAG

CCAACAGGATTCCTGAGCTGAAATGCAGATGAACCACATTCAAGGAAGAACCTTCTGTCC

CAGCTTTGCAGAATGAAAAGCTTTCCTGCTTGGCAGTTATTCTTCCACAAGAGAGGGCTT

TCTCAGGACCTGGTTGCTACTGGTTCGGCAACTGCAGAAAATGTTCCTCCCTTGTGGCTT

CCTCAGCTCCTGCCCTTGGCCTGAAGTCCCAGCATTGATGACAGCGCCTCATCTTCAGCT

TTTGTGCTCCCCTTTGCCTAAACCGTATGGCCTCCCGTGCATCTGTACTCACCCTGTACG

ACAAACACATTACATTATTAAA

Clone 2918.8

CCCCATCAGATCCATCAGGTCTGAGCTGTGTTGATTACCACTACTTTTCCCTTCGTCTCA

ATTATGTCTTGCAAGAAGTCTTTCGCGATCCCCGGAGACCTTCGGGTAGCAACTGTAACC

TTGATGCTGGCGATTCTGAGCTCCTACTTGGCTGAGGGCAGAGACTCTCCCGAGGATTTC

GTGTACCAGTTTAAGGGCCTGTGCTACTTCACCAACGGGACGGGGCGCGTGCGGGGTGTG

ACCAGACACATCTATAACCGAGAGGAGTACGTGCGCTTCGACAGCGACGTGGGGGTGTAC

CGGGCAGTGACGACGCAGGGGCGGCTTGTTGCCGAGTACTGGAACAGCCACAAGCAAGTC

CTGGAGGGGGCCCGGCCGTCGGTGGACAGGGTGTGCAGACACAACTACGAGGTGGCGTAC

CGCGGGATCCTGCAGAGGAGAGTGGAGCCCACAGTGACCATCTCCCCATCCAGGACAGAG

GCCCTCAACCACCACAACCTGCTGATCTGCTCGGTGACAGATTTCTATCCAAGCCAGATC

AAAGTCCGGTGGTTTCGGAATGATCAGGAGGAGACAGCCGGCGTTGTGTCCACCCCCCTC

ATTAGGAACGGTGACTGGACCTCCCAGATCCTGGTGATGCTGGAAATGACTCCCCAGCGT

GGAGATGTCTACACCTGCCACGTGGAGCACCCCAGCCTCCA

Comparison of the amino acid sequences encoded by these clones with published amino acid sequence for HLA-DRβ and HLA-DCβ antigens indicated the clones were, respectively, HLA-DRβ and HLA-DCβ clones. $^{32}$P-labeled probes were made from these clones by nick translation.

EXAMPLE 4

Preparation of SBβ cDNA Clone

An SBβ cDNA clone pDB114 (685 bp insert), was identified by screening the above-described λ cDNA library with two different hybridization probes. One was a synthetic oligonucleotide 28-mer,

TCTGTGGAGTGGGCATCTTCATGCACAG based on the published sequence of an SBβ clone (Roux-Dosseto, M., et al, *Proc Natl Acad Sci* (1983) 80:6036-6040) and the other was the DCβ clone hybridized to the plaque filters under conditions of low stringency. The sequence of the oligomer was chosen as maximally divergent between SBβ and DCβ and in an area, the transmembrane region, unlikely to vary between different SBβ alleles. The longest of the clones isolated in this screening, pDB114, was further analyzed by using it as a hybridization probe on genomic blots of γ ray-induced deletion HLA mutants (Kavathas, P., et al, *Nature* (1981) 293:747-749) and definitively identified by comparing the nucleotide sequence with the published SBβ clone sequence. The clone pDB114, sequence given below, showed 100% homology with the published SBβ sequence. This clone was used as a hybridization probe to rescreen the cDNA library in order to identify a full-length cDNA clone with a cDNA insert of ~1,200 bp.

Human HLA SB-βcDNA Sequence

```
       Val Arg Trp Phe Leu Asn Gly Gln Glu Glu Thr Ala Gly Val Val Ser Thr Asn Leu
  1:   AAGTCCGATGGTTCCTGAATGGACAGGAGGAAACAGCTGGGGTCGTGTCCACCAACCTG

Ile Arg Asn Gly Asp Trp Thr Phe Gln Ile Leu Val Met Leu Glu Met Thr Pro Gln Gln
 61:   ATCCGTAATGGAGACTGGACCTTCCAGATCCTGGTGATGCTGGAAATGACCCCCCAGCAG

Gly Asp Val Tyr Thr Cys Gln Val Glu His Thr Ser Leu Asp Ser Pro Val Thr Val Glu
121:   GGAGATGTCTACACCTGCCAAGTGGAGCACACCAGCCTGGATAGTCCTGTCACCGTGGAG

Trp Lys Ala Gln Ser Asp Ser Ala Arg Ser Lys Thr Leu Thr Gly Ala Gly Gly Phe Val
181:   TGGAAGGCACAGTCTGATTCTGCCCGGAGTAAGACATTGACGGGAGCTGGGGGCTTCGTG

Leu Gly Leu Ile Ile Cys Gly Val Gly Ile Phe Met His Arg Arg Ser Lys Lys Val Gln
241:   CTGGGGCTC ATCATCTGTGGAGTGGGCATCTTCATGCACAGGAGGAGCAAGAAAGTTCAA

Arg Gly Ser Ala
301:   CGAGGATCTGCATAAACAGGGTTCCTGAGCTCACTGAAAAGACTATTGTGCCTTAGGAAA

361:   AGCATTTGCTGTGTTTCGTTAGCATCTGGCTCCAGGACAGACCTTCAACTTCCAAATTGG

421:   ATACTGCTGCCAAGAAGTTGCTCTGAAGTCAGTTTCTATCATTCTGCTCTTTGATTCAAA

481:   GCACTGTTTCTCTCACTGGGCCTCCAACCATGTTCCCTTCTTCTTAGCACCACAAATAAT

541:   CAAAACCCAACATGACTGTTTGTTTTCCTTAAAAATAATGCACCAAATCATCTCTCATCA

601:   CTTTTCTCTGAGGGTTTTAGTAGACAGTAGGAGTTAATAAAGAAGTCGGAATTCGAGCTC

661:   GCCCGGGGATCCTCTAGAGTCGACCT
```

EXAMPLE 5

Preparation of DCα cDNA Clone

A DCα cDNA (1060 bp insert) was identified by screening the above-described λ cDNA library with two different hybridization probes. One was a synthetic 18-mer oligonucleotide,

TGTCTGGAAGCACCAACT, based on the published sequence of a DCα clone (Auffray, C., et al, *Nature* (1984) 308:327–333) and the other was the DRα probe hybridized to the λ plaque filters under conditions of low stringency. The sequence of the oligomer was chosen as maximally divergent between DCα and DRα and SBα. Any clones which hybridized to both probes were further analyzed for full-length cDNA inserts. The identity of the putative DCα clone was confirmed by comparing the genomic blot patterns with published reports, mapping the gene by genomic blotting with HLA deletion mutants (Kavathas, P., et al, *Nature* (1981) 293:747–749) and, most definitively, by comparing its nucleotide sequence, given below, with published DCα clone sequences. The homology is 98.5% with the Auffray, C., et al sequence and 93.4% with another (Schenning, L., et al, *EMBO* (1984) 3:447–452); the small degree of variation is attributed to allelic polymorphism and it was concluded that this cDNA clone encodes the DCα chain of the LG2 cell line. RFLPs in the DCα loci have been observed with a substantial number of restriction enzymes.

Human HLA DC-α cDNA Clone (1060 bp)

```
                  +1
       Ala Leu Thr Thr Val Met Ser Pro Cys Gly Gly Glu Asp Ile Val Ala Asp His Val Ala
  1:   GCCCTGACCACCGTGATGAGCCCCTGTGGAGGTGAAGACATTGTGGCTGACCACGTTGCC

Ser Cys Gly Val Asn Leu Tyr Gln Phe Tyr Gly Pro Ser Gly Gln Tyr Thr His Glu Phe
 61:   TCTTGTGGTGTAAACTTGTACCAGTTTTACGGTCCCTCTGGCCAGTACACCCATGAATTT

Asp Gly Asp Glu Glu Phe Tyr Val Asp Leu Glu Arg Lys Glu Thr Ala Trp Arg Trp Pro
121:   GATGGAGATGAGGAGTTCTACGTGGACCTGGAGAGGAAGGAGACTGCCTGGCGGTGGCCT

Glu Phe Ser Lys Phe Gly Gly Phe Asp Pro Gln Gly Ala Leu Arg Asn Met Ala Val Ala
181:   GAGTTCAGCAAATTTGGAGGTTTTGACCCGCAGGGTGCACTGAGAAACATGGCTGTGGCA

Lys His Asn Leu Asn Ile Met Ile Lys Arg Tyr Asn Ser Thr Ala Ala Thr Asn Glu Val
241:   AAACACAACTTGAACATCATGATTAAACGCTACAACTCTACCGCTGCTACCAATGAGGTT

Pro Glu Val Thr Val Phe Ser Lys Ser Pro Val Thr Leu Gly Gln Pro Asn Thr Leu Ile
301:   CCTGAGGTCACAGTGTTTTCCAAGTCTCCCGTGACACTGGGTCAGCCCAACACCCTCATT

Cys Leu Val Asp Asn Ile Phe Pro Pro Val Val Asn Ile Thr Trp Leu Ser Asn Gly Gln
361:   TGTCTTGTGGACAACATCTTTCCTCCTGTGGTCAACATCACATGGCTGAGCAATGGGCAG

Ser Val Thr Glu Gly Val Ser Glu Thr Ser Phe Leu Ser Lys Ser Asp His Ser Phe Phe
421:   TCAGTCACAGAAGGTGTTTCTGAGACCAGCTTCCTCTCCAAGAGTGATCATTCCTTCTTC

Lys Ile Ser Tyr Leu Thr Phe Leu Pro Ser Ala Asp Glu Ile Tyr Asp Cys Lys Val Glu
481:   AAGATCAGTTACCTCACCTTCCTCCCTTCTGCTGATGAGATTTATGACTGCAAGGTGGAG

His Trp Gly Leu Asp Gln Pro Leu Leu Lys His Trp Glu Pro Glu Ile Pro Ala Pro Met
541:   CACTGGGGCCTGGACCAGCCTCTTCTGAAACACTGGGAGCCTGAGATTCCAGCCCCTATG

Ser Glu Leu Thr Glu Thr Val Val Cys Ala Leu Gly Leu Ser Val Gly Leu Val Gly Ile
601:   TCAGAGCTCACAGAGACTGTGGTCTGCGCCCTGGGGTTGTCTGTGGGCCTCGTGGGCATT

Val Val Gly Thr Val Phe Ile Ile Gln Gly Leu Arg Ser Val Gly Ala Ser Arg His Gln
661:   GTGGTGGGCACTGTCTTCATCATCCAAGGCCTGCGTTCAGTTGGTGCTTCCAGACACCAA

Gly Pro Leu
721:   GGGCCATTGTGAATCCCATCCTGGAAGGGAAGGTGCATCGCCATCTACAGGAGCAGAAGA

781:   GTGGACTTGCTACATGACCTAGCACTATTCTCTGGCCCCGATTTATCATATCCCTTTTCT

841:   CCTCCAAATATTTCTCCTCTCACCTTTTCTCTGGGACTTAAGCTGCTATATCCCCTCAGA

901:   GCTCACAAATGTCTTTACATTCTTTCCCTGACCTCCTGATTTTTTTTTTCTTTTCTCAAA

961:   TGTTACCTACAAAGACATGCCTGGGGTAAGCCACCCGGCTACCTAATTCCTCAGTAACCT

1021:  CCATCTATAATCTCCAAGGAAGCAACAAATTCCTTTTATG
```

EXAMPLE 6

Determination of HLA-DRα Restriction Fragment Length Polymorphism Using BglII and HLA-Dp34 Hybridization Probe

Digestion of DNA with BglII

Samples of DNA were obtained from nucleated cells of five unrelated individuals and four children of two of the individuals. Five to 10 μg of each DNA sample were digested for 1–2 hr at 37° C. with 4(15') units of BglII per μg of DNA. The buffer was 60 mM NaCl, 6 mM Tris HCl (pH 7.5), 6 mM MgCl₂, 6 mM 2-mercaptoethanol.

Genomic Blotting of Restriction Digests with HLA-Dp34 Probe

Between five and ten μg of each restriction enzyme digested DNA was fractionated according to size by electrophoresis in a 0.6% agarose gel for approximately 500 V-hr. Electrophoresis buffer was 40.0 mM Tris, 2.5 mM EDTA, 25.0 mM acetate, pH 8.2. After electrophoresis the DNA was stained with 0.5 μg/ml ethidium bromide and the gel was photographed. The DNA in the gel was depurinated with a 15' wash in 75 mM HCl at room temperature. DNA was denatured with 2 successive 15' washes in 0.5 M NaOH +1.5 M NaCl at room temperature. DNA was neutralized with 2 successive 15' washes in 1.5M Tris-Cl pH 7.4 +3.0 M NaCl at room temperature. DNA was transferred from the gel to nitrocellulose (0.45 micron pore size) by blotting with 20×SSPE (20×SSPE=3.6 M NaCl, 200.0 mM phosphate, 20.0 mM Na$_2$EDTA, pH 7.0) for 3 hr at room temperature. DNA was bound to the nitrocellulose by baking at 80° C. for 2 hr in a vacuum oven.

The nitrocellulose filter was placed in a heat sealable plastic bag and was prehybridized for 8 hr at 42° C. in a solution composed of 50% formamide, 5×SSPE, 200 μg/ml sheared denatured salmon sperm DNA, 0.1% SDS, and 2×Denhardt's solution. After 8 hr, the prehybridization solution was removed from the ba9 and replaced with a solution composed of 50% formamide, 5×SSPE, 100 μg/ml sheared denatured salmon sperm DNA, 0.1% SDS, 2×Denhardt's solution, 10% sodium dextran sulphate, and 1–5×10$^6$ com denatured $^{32}$P-labeled HLA-Dp34 probe. The probe was labeled using the nick translation reaction of Rigby, et al, supra, to specific activities of 5×10$^8$–1×10$^9$ cpm/μg. The bag was resealed and the nitrocellulose filter was hybridized with the probe for 18–24 hr at 42° C.

The nitrocellulose filter was removed from the bag and washed in 4 successive changes (15' each) of 2×SSPE, 0.17% SDS at room temperature. The filter was then washed in 4 successive changes (15' each) of 0.1×SSPE, 0.1% SDS at 50° C.

The filter was air dried, covered with Saran Wrap and autoradiographed with Kodak XAR-5 film with an intensifying screen for 18–72 hr at −80° C. FIG. 1 is a copy of the resulting autoradiograph.

Discussion of Autoradiograph

The autoradiograph shows that BglII produced three different restriction fragments in the tests: 3.8, 4.2, and 4.5 kb in length. This clearly evidences that the HLA-Dp34 locus is polymorphic and that there are at least three alleles of this gene.

Lane 1 of the autoradiograph is a blot of the cell line CA. Lanes 3 and 2 of the autoradiograph are the blots of the cell line 6.3.6 and its parent T5-1, respectively. These are the blots discussed in Example 1 that map the HLA-Dp34 gene to chromosome 6 at the site defined by the 6.3.6 deletion.

Lanes 4 and 5 are blots of the mother and father of a family and lanes 6–9 are blots of the children of those parents. Lane 4 is the father's blot and his haplotype is designated A/B. Both chromosome A and chromosome B have the same restriction fragment (4.2 kb). Lane 5 is the mother's blot and her haplotype is designated C/D. Each chromosome C and D has a different restriction fragment (4.2 kb and 4.5 kb, respectively). In the offspring of these parents the maternal 4.2 kb genomic fragment segregates with the serologically defined D haplotype.

EXAMPLE 7

HLA-Dp34 Typing Based on RFLP Using HLA-Dp34 Hybridization Probe and the Restriction Endonuclease BqlII A sample of peripheral blood is obtained from an individual and the HLA DNA is extracted therefrom using the methods described in Example 6. The DNA is digested using BglII and a genomic blot of the digest is made using the HLA-Dp34 as described in Example 6. The restriction fragment pattern of the resulting autoradiograph is compared to the restriction fragment patterns described in Example 6 (FIG. 1) for HLA-Dp34 to determine the individual's HLA-Dp34 type.

EXAMPLE 8

Figure 2:
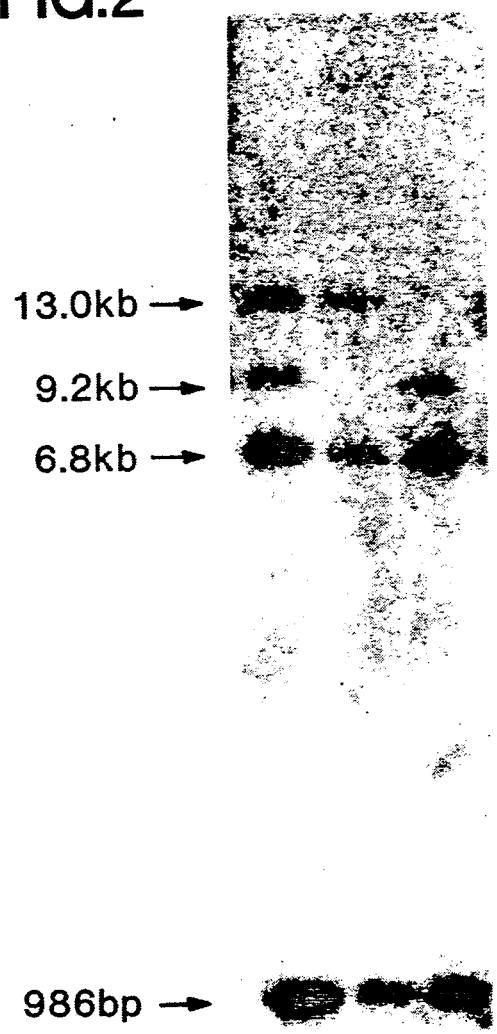
FIG. 2 is the autoradiograph described in Example 8.

Restriction Fragment Length Polymorphisms Detected with EcoRV and HLA-Dp34 (DRα) Probe Ten μg samples of DNA were obtained from three individuals and digested for 1–4 hr at 37° C. with 80 units of EcoRV. The buffer was 0.15 M NaCl, 6 mM Tris HCl (pH 7.9), 6 mM MgCl$_2$, 6 mM 2-mercaptoethanol. Genomic blotting and hybridization of restriction digested DNAs were carried out as in Example 6. An autoradiograph was prepared of the genomic blotting patterns as in Example 6. FIG. 2 is a copy of the resulting autoradiograph.

Figure 3:
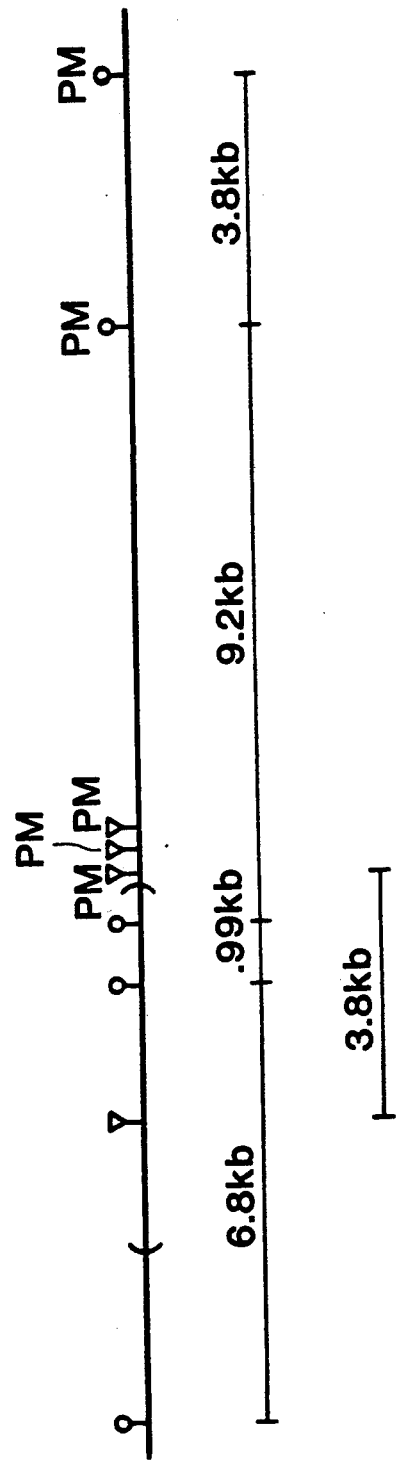
FIG. 3 is a restriction map of the HLA-DR locus showing the location of polymorphic restriction sites for the enzymes BglII and EcoRV detected with the probe of Example 1.

As seen in FIG. 2, all three individuals possess a 986 bp and a 6.8 kb EcoRV fragment (nonpolymorphic fragments). In addition, every individual possesses either a 9.2 kb or a 13.0 kb EcoRV fragment, or both (polymorphic fragments). FIG. 3 is a map diagramming the location of the polymorphic restriction sites for BglII (Example 6) and EcoRV detected with the HLA-Dp34 probe.

EXAMPLE 9

Determination of Restriction Fragment Length Polymorphism in Class II Locus Using BglII and Hybridization Probe p29G8

Figure 4:
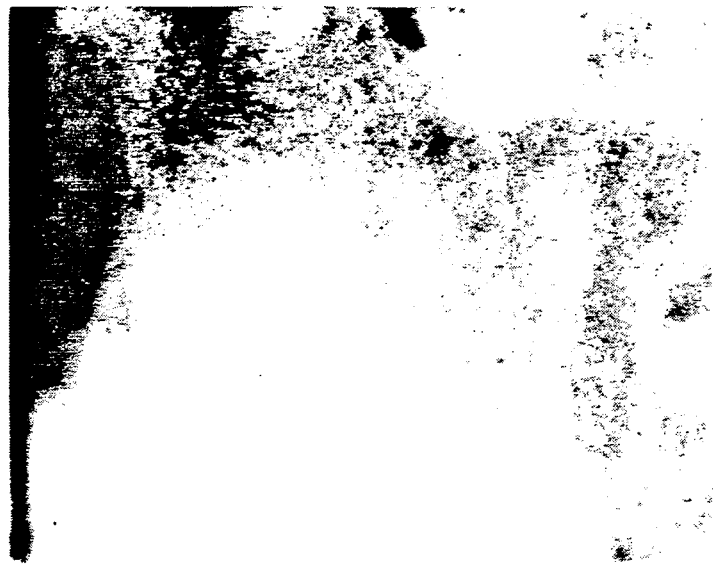
FIG. 4 is the autoradiograph described in Example 9.
Figure 4:

Ten μg samples of DNA from five individuals of one family and five individuals of a second family were digested with BglII using the procedure of Example 6. The digests were subjected to electrophoresis, genomic blotting and hybridization by the procedure of Example 6 except that the nick translated p29G8 probe of Example 2 was used instead of the HLA-Dp34 probe. FIG. 4 is an autoradiograph of the resulting genomic blotting patterns. Lanes 1–5 are the patterns for the five individuals of the first family and Lanes 6–10 are the patterns of the five individuals of the second family. As seen in FIG. 4 three types ("alleles") were observed in the samples characterized by 2.2 kb, 2.4 kb, and 4.4 kb fragments. In the HLA typed families of this example the polymorphic BglII fragments segregate with serologically defined parental haplotypes.

EXAMPLE 10

Use of HLA-B7 Hybridization Probe to Evaluate HLA Restriction Fragment Length Polymorphisms in Human Pedigrees An HLA-B7 cDNA clone was obtained from Sherman M. Weissman, Dept of Human Genetics, Yale University School of Medicine. This clone is described in Sood, et al, supra.

Figure 5:
FIGS. 5, 6, and 7 are the autoradiographs
Figure 6:
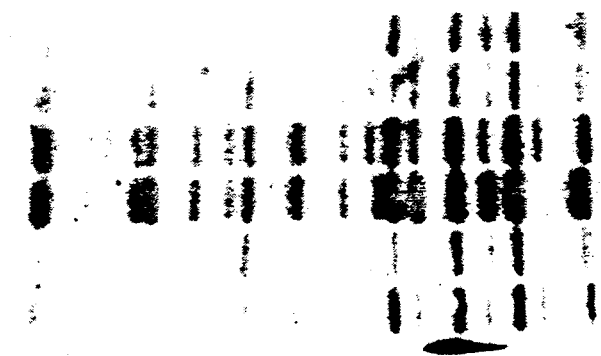
Figure 7:

DNA samples from the father, mother, and four children of an HLA typed family and in two instances DNA from one or two individuals (designated X and Y) unrelated to that family were digested according to Example 6 with either HindIII, PvuII, or BamHl. Genomic blots of the digests were made as in Example 6 using the $^{32}P$ nick translated HLA-B7 clone as a hybridization probe. FIGS. 5, 6 and 7 are copies of the resulting autoradiographs. The father's haplotype is designated A/D and the mother's haplotype is designated E/F. These autoradiographs indicate that the probe is a multilocus probe that hybridizes to more than one HLA locus. Nonetheless, several polymorphic bands, segregating in the pedigree, are present for each enzyme used. Moreover, the bands segregate with the serologically defined HLA loci so that given fragments may be assigned to an individual chromosome.

Exclusionary paternity determinations may be made using autoradiographs such as FIGS. 5, 6 and 7. An exclusionary pattern would involve a restriction fragment pattern which could not be inherited from the mother and alleged father. Such a pattern would be one in which the child has a fragment that neither the mother nor alleged father has. Positive paternity determinations using RFLPs will depend upon the frequency of the RFLPs in the general population. In such determinations one calculates the probability that the putative father contributed the RFLP that is observed and compares it with the probability that any random male would contribute the RFLP to the child.

EXAMPLE 11

Use of BglII and HLA-Dp34 (DRα) Probe to Evaluate Linkage and Association Between HLA-DRα and Insulin Dependent Diabetes Mellitus (IDDM) in Six Families Genetic susceptibility to a number of diseases shows linkage as well as association in population studies with specific serologically defined variants of the HLA class I and class II loci. These loci encode cell surface glycoproteins which mediate a variety of immune functions. The association of many diseases with an autoimmune component, such as IDDM with serologically defined class II variants (HLA-DR types) suggests the existence of disease susceptibility genes in linkage disequilibrium with specific serologic markers. It is not yet known whether the class II gene products are themselves involved in disease causation and, if so, whether the variants of the polymorphic sequences which form the basis of immunologic typing are the same ones that confer disease susceptibility.

The genetic basis of IDDM susceptibility is complex; about 70% of the genetic component is thought to be HLA-linked and the penetrance, as revealed by monozygotic twin studies, is about 50%. IDDM has been associated in population studies with the DR3 and/or DR4 specificities, about 90% of IDDM patients are either DR3 and/or DR4, compared to about 55% of control individuals. The relatively low proportion of DR3 and DR4 individuals who develop IDDM may reflect the incomplete penetrance as well as the apparent heterogeneity within the serologically defined DR types, such as DR3 and DR4 loci. Genetic heterogeneity within the serologically defined DR types has been demonstrated by a variety of cellular, biochemical, and molecular techniques. Thus, new DNA markers could prove more informative than serological DR3 or DR4 markers if (1) they subdivide existing serological types, or (2) they identify IDDM susceptibility chromosomes that are neither of the DR3 nor DR4 type.

Ten μg samples of DNA from the individuals of six different families having histories of IDDM were digested with BglII, blotted, and hybridized with the HLA-Dp34 probe by the procedure of Example 6. Autoradiographs of the resulting genomic blotting patterns were made.

Figure 8:
FIGS. 8 and 9 are the autoradiographs described in Example 11.

FIG. 8 is an autoradiograph of eight individuals of one of the families. The father's pattern appears in Lane 1, the mother's in Lane 2 and six children in Lanes 3-8. The father has the 4.2 kb fragment (derived from chromosome 6 haplotype A) and the 3.8 kb fragment from haplotype B. The mother has the 4.2 kb fragment (haplotype C) and the 4.5 kb fragment (haplotype D). The three affected (IDDM) children have either two copies of the 4.2 kb fragment (haplotype A/C, Lanes 3 and 5) or one copy of the 4.2 kb fragment (haplotype A) and one copy of the 4.5 kb fragment (haplotype D) in Lane 4. One unaffected child (Lane 7) has two copies of the 4.2 kb fragment (haplotype A/C). The two unaffected children (Lanes 6 and 8) both have the 3.8 kb fragment (haplotype B) and the 4.5 kb fragment (haplotype D). Thus, the 4.2 kb fragment is linked in this family to a disease susceptibility gene for IDDM. Three of the four children with the 4.2 kb fragment exhibit IDDM, indicating an incomplete penetrance (genetic predisposition) of the disease allele.

In four of the other five families tested the segregation pattern was consistent with linkage of the 4.2 kb BglII fragment to the IDDM disease susceptibility allele.

Figure 9:
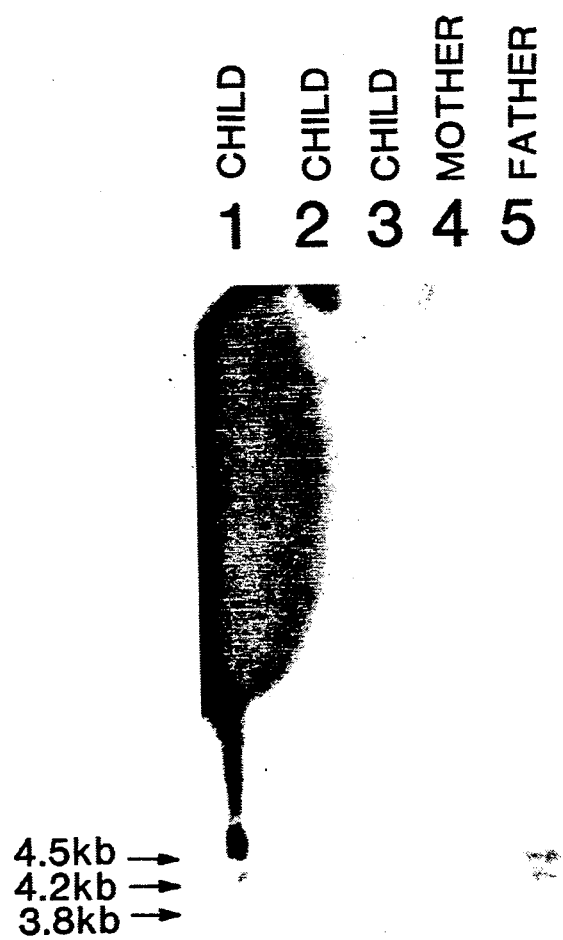

FIG. 9 is an autoradiograph of five individuals of the sixth family. The father's pattern appears in Lane 5, the mother's in Lane 4 and the three children in Lanes 1-3. In this family, disease susceptibility appeared to be linked to the 4.5 kb BglII fragment. Here, the affected father has a 4.5 kb fragment (haplotype A) and 4.2 kb fragment (haplotype B) and the mother has a 4.5 kb fragment (haplotype D) and a 3.8 kb fragment (haplotype C). Of the three children, only one has IDDM (Lane 3) and he inherited the 4.5 kb fragment from the father and the 3.8 kb fragment from the mother. Therefore, in this family the 4.5 kb BglII fragment is linked to the disease susceptibility allele on the paternal haplotype A.

In summary, five of the six probands in this set of diabetes families had at least one copy of the 4.2 kb BglII fragment. In a sample of unrelated control individuals, 4/16 individual DNA samples had the 4.2 kb fragment, suggesting an increased relative risk (RR) for IDDM associated with the 4.2 kb fragment due, presumably, to linkage disequilibrium between the polymorphic BglII site and a linked IDDM susceptibility allele.

$$RR \text{ (relative risk)} = \frac{(.834) \times (.75)}{(.25)(.167)} = 14$$

By comparison, the relative risk for the serologically defined HLA-DR3 = 3.3 and for HLA-DR4 = 6.4.

The analysis of DNA from HLA-DR typed individuals and from families has shown that the DRα BglII 8.2 kb fragment is associated with a subset of DR3 types (Table 2). The 4.2 kb fragment is present in 80% of IDDM DR3 chromosomes but only in 40% of control DR3 chromosomes. Thus, the 4.2 kb fragment is a marker for DR3 associated genetic susceptibility to IDDM but not for DR4 associated susceptibility. The subset of DR3 chromosomes (HLA B8 DR3) that have the 4.2 kb marker is associated with genetic predisposition to a variety of autoimmune diseases such as myasthemia gravis, SLE, Graves disease, etc. By using more restriction endonucleases and more probes, it should be possible to generate a significantly higher value than the one indicated by these data with the HLA-DR probe and BglII.

TABLE 2

Frequency of DR3 Individuals with the DRα BglII 4.2 kb Fragment

|  | Control | Diabetic |
|---|---|---|
| B8 DR3 | 6/6 | 17/17 |
| Bx DR3 | 1/9 | 1/8 |
| DR3 | 7/15 | 18/25 |

EXAMPLE 12
Identification of RFLPs Associated with IDDM Using the HLA-DRβ and HLA-DCβ Probes Genomic DNA from IDDM patients and random normal patients was extracted and pooled separately. Both pools were digested with 14 different restriction endonucleases (BglII, BamHI, EcoRV, KpnI, EcoRI, PstI, HindIII, StaI, SacI, XbaI, PvuII, MspI, TaqI, RsaI) and analyzed by Southern blotting, hybridization with the above described DRβ and DCβ probes and autoradiography as above. The resulting Southern blot patterns were compared for the presence of specific restriction fragments whose frequency was increased in the IDDM population relative to the normal population. Once such fragments were identified, genomic blot analysis was performed on DNA samples for HLA-DR typed IDDM families to examine segregation pattern and assign the restriction fragment to DR-typed chromosomes. Analysis of such families, as well as the analysis of DR-typed homozygous typing cells, and DR-typed control and IDDM individuals allowed the correlation of polymorphic restriction fragments with DR type. The data for the TaqI (DRβ) and the RsaI (DCβ) fragments which are increased among IDDM patients are shown in Table 3 below.

TABLE 3

Frequency of Individuals With Specific DCβ and DRβ Restriction Fragments

|  | IDDM (Probands and Controls (n = 33) | unrelated (n = 44)) |
|---|---|---|
| DCβ-RsaI 2.7 kb |  |  |
| DR3: | 1.00 (10/10) | 1.00 (25/25) |
| non DR3: | 0.0 (0/23) | 0.0 (0/19) |
| DCβ-RsaI 1.5 kb |  |  |
| DR4: | 0.76 (13/17) | 0.90 (27/30) |
| non DR4: | 0.0 (0/16) | 0.29 (4/14) |

|  | Controls (n = 23) | IDDM (Probands and unrelated (n = 32)) |
|---|---|---|
| DRβ-TaqI 7.3 kb |  |  |
| DR3: | 1.00 (11/11) | 1.00 (16/16) |
| non DR3: | 0.25 (3/12) | 0.25 (4/16) |
| DRβ-TaqI 2.6 kb |  |  |
| DR4: | 1.00 (6/6) | 1.00 (22/22) |
| non DR4: | 0.24 (4/17) | 0.4 (4/10) |
| DRβ-TaqI 10 kb |  |  |
| DR3: | 0.55 (6/11) | 0.9 (9/10) |
| non DR3: | 0.17 (2/12) | 0.09 (1/11) |

The RsaI 2.7 kb DCβ fragment is correlated with the DR3 specificity while the 1.5 kb DCβ fragment is correlated with DR4. Those DR4 individuals who are not 1.5 kb have an allelic 1.8 kb fragment. The 1.5 kb fragment is also found in IDDM patients who are not DR4. The TaqI 7.3 kb DR8 is correlated with DR3 and the 2.6 kb DRβ fragment with DR4. The TaqI 12 kb DRβ subdivides the DR3 type such that 90% of IDDM DR3 patients have this marker but only 55% of control DR3 individuals have it.

In addition, a 5.0 kb PstI (DCβ) fragment was increased among IDDM patients. Specific KpnI, HindIII, StuI, SacI, and XbaI DCβ fragments were also increased in IDDM patients. These latter observations were made only on pooled DNA samples from IDDM and control individuals.

Modifications of the methods and compositions described above that are obvious to those of ordinary skill in genetic engineering, genetics, molecular biology, biochemistry, and/or immunology are intended to be within the scope of the following claims.

I claim:

1. A DNA probe that is specific to a single Class II HLA locus comprising a labeled DNA sequence that is substantially complementary to the DNA sequence at said locus.

2. The probe of claim 1 wherein the locus is a DRα locus.

3. The probe of claim 1 wherein the locus is the DRα locus and the probe includes the nucleotide sequence

| ATCATAGCTG | TGCTGATGAG | CGCTCAGGAA | TCATGGGCTA | TCAAAGAAGA |
| ACATGTGATC | ATCCAGGCCG | AGTTCTATCT | GAATCCTGAC | CAATCAGGCG |
| AGTTTATGTT | TGACTTTGAT | GGTGATGAGA | TTTTCCATGT | GGATATGGCA |
| AAGAAGGAGA | CGGTCTGGCG | GCTTGAAGAA | TTTGGACGAT | TTGCCAGCTT |
| TGAGGCTCAA | GGTGCATTGG | CCAACATAGC | TGTGGACAAA | GCCAACCTGG |
| AAATCATGAC | AAAGCGCTCC | AACTATACTC | CGATCACCAA | TGTACCTCCA |
| GAGGTAACTG | TGCTCACGAA | CAGCCCTGTG | GAACTGAGAG | AGCCCAACGT |
| CCTCATCTGT | TTCATCGACA | AGTTCACCCC | ACCAGTGGTC | AATGTCACGT |
| GGCTTCGAAA | TGGAAAACCT | GTCACCACAG | GAGTGTCAGA | GACAGTCTTC |

-continued

| | | | | |
|---|---|---|---|---|
| CTGCCCAGGG | AAGACCACCT | TTTCCGCAAG | TTCCACTATC | TCCCCTTCCT |
| GCCCTCAACT | GAGGACGTTT | ACGACTGCAG | GGTGGAGCAC | TGAGGCTTGG |
| ATGAGCCTCT | TCTCAAGCAC | TGGGAGTTTG | ATGCTCCAAG | CCCTCTCCCA |
| GAGACTACAG | AGAACGTGGT | GTGTGCCCTG | GGCCTGACTG | TGGGTCTGGT |
| GGGCATCATT | ATTGGGACCA | TCTTCATCAT | CAAGGGAGTG | CGCAAAAGCA |
| ATGCAGCAGA | ACGCAGGGGG | CCTCTGTAAG | GCACATGGAG | GTGATGATGT |
| TTCTTAGAGA | GAAGATCACT | GAAGAAACTT | CTGCTTTAAT | GACTTTACAA |
| AGCTGGCAAT | ATTACAATCC | TTGACCTCAG | TGAAAGCAGT | CATCTTCAGC |
| GTTTTCCAGC | CCTATAGCCA | CCCCAAGTGT | GGTTATGCCT | CCTCGATTGC |
| TCCGTACTCT | AACATCTAGC | TGGCTTCCCT | GTCTATTGCC | TTTTCCTGTA |
| TCTATTTTCC | TCTATTTCCT | ATCATTTTAT | TATCACCATG | CAATGCCTCT |
| GGAATAAAAC | ATACAGGAGT | CTGTCTCTGC | TATGGAATGC | CCCATGGGGC |
| TCTCTTGTGT | ACTTATTGTT | TAAGGTTTCC | TCAAACTGTG | ATTTTTCTG. |

4. A substantially pure single stranded DNA probe that is complementary to a single Class II HLA locus.

5. A substantially pure single stranded DNA probe of claim 4 wherein the HLA locus is the DRα locus.

6. The substantially pure DNA probe of claim 4 wherein the HLA locus is the DRα locus and the sequence is 7. A substantially pure DNA segment which is complementary to at least a fragment of at least one β-chain Class II HLA locus involved in polymorphism.

8. A substantially pure DNA segment which is complementary to at least a fragment of at least one α-chain Class II HLA locus involved in polymorphism.

9. A substantially pure DNA segment which is complementary to at least a fragment of at least one Class II HLA locus involved in polymorphism.

* * * * *

| | | | | |
|---|---|---|---|---|
| ATCATAGCTG | TGCTGATGAG | CGCTCAGGAA | TCATGGGCTA | TCAAAGAAGA |
| ACATGTGATC | ATCCAGGCCG | AGTTCTATCT | GAATCCTGAC | CAATCAGGCG |
| AGTTTATGTT | TGACTTTGAT | GGTGATGAGA | TTTTCCATGT | GGATATGGCA |
| AAGAAGGAGA | CGGTCTGGCG | GCTTGAAGAA | TTTGGACGAT | TTGCCAGCTT |
| TGAGGCTCAA | GGTGCATTGG | CCAACATAGC | TGTGGACAAA | GCCAACCTGG |
| AAATCATGAC | AAAGCGCTCC | AACTATACTC | CGATCACCAA | TGTACCTCCA |
| GAGGTAACTG | TGCTCACGAA | CAGCCCTGTG | GAACTGAGAG | AGCCCAACGT |
| CCTCATCTGT | TTCATCGACA | AGTTCACCCC | ACCAGTGGTC | AATGTCACGT |
| GGCTTCGAAA | TGGAAAACCT | GTCACCACAG | GAGTGTCAGA | GACAGTCTTC |
| CTGCCCAGGG | AAGACCACCT | TTTCCGCAAG | TTCCACTATC | TCCCCTTCCT |
| GCCCTCAACT | GAGGACGTTT | ACGACTGCAG | GGTGGAGCAC | TGAGGCTTGG |
| ATGAGCCTCT | TCTCAAGCAC | TGGGAGTTTG | ATGCTCCAAG | CCCTCTCCCA |
| GAGACTACAG | AGAACGTGGT | GTGTGCCCTG | GGCCTGACTG | TGGGTCTGGT |
| GGGCATCATT | ATTGGGACCA | TCTTCATCAT | CAAGGGAGTG | CGCAAAAGCA |
| ATGCAGCAGA | ACGCAGGGGG | CCTCTGTAAG | GCACATGGAG | GTGATGATGT |
| TTCTTAGAGA | GAAGATCACT | GAAGAAACTT | CTGCTTTAAT | GACTTTACAA |
| AGCTGGCAAT | ATTACAATCC | TTGACCTCAG | TGAAAGCAGT | CATCTTCAGC |
| GTTTTCCAGC | CCTATAGCCA | CCCCAAGTGT | GGTTATGCCT | CCTCGATTGC |
| TCCGTACTCT | AACATCTAGC | TGGCTTCCCT | GTCTATTGCC | TTTTCCTGTA |
| TCTATTTTCC | TCTATTTCCT | ATCATTTTAT | TATCACCATG | CAATGCCTCT |
| GGAATAAAAC | ATACAGGAGT | CTGTCTCTGC | TATGGAATGC | CCCATGGGGC |
| TCTCTTGTGT | ACTTATTGTT | TAAGGTTTCC | TCAAACTGTG | ATTTTTCTG. |